(12) United States Patent
Yang et al.

(10) Patent No.: US 7,135,343 B2
(45) Date of Patent: Nov. 14, 2006

(54) BIOMOLECULE RESISTANT AND THEIR METHODS OF USE IN ASSAYS

(75) Inventors: Dan-Hui Yang, Sunnyvale, CA (US); Namyong Kim, North Andover, MA (US); Janelle Gunther, Mountview, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 709 days.

(21) Appl. No.: 10/173,255

(22) Filed: Jun. 17, 2002

(65) Prior Publication Data

US 2003/0232345 A1 Dec. 18, 2003

(51) Int. Cl.
*G01N 33/552* (2006.01)
*G01N 33/545* (2006.01)
*C07K 1/04* (2006.01)

(52) U.S. Cl. ............ 436/527; 436/531; 530/402; 530/408; 530/409; 530/410; 530/411; 530/811

(58) Field of Classification Search ............ 436/527, 436/531; 530/402, 408, 409, 410, 411, 811
See application file for complete search history.

(56) References Cited

U.S. PATENT DOCUMENTS

| | | | |
|---|---|---|---|
| 5,175,027 A | 12/1992 | Holmes-Farley et al. | |
| 5,405,766 A | 4/1995 | Kallury et al. | |
| 5,412,087 A | 5/1995 | McGall et al. | |
| 5,688,642 A | 11/1997 | Chrisey et al. | |
| 5,856,016 A | 1/1999 | Takahashi et al. | |
| 6,039,897 A * | 3/2000 | Lochhead et al. | 264/1.24 |
| 6,235,488 B1 | 5/2001 | Tom-Moy et al. | |
| 6,329,209 B1 | 12/2001 | Wagner et al. | |
| 2002/0182413 A1* | 12/2002 | Kunitake et al. | 428/403 |
| 2005/0064204 A1* | 3/2005 | Lalli et al. | 428/428 |

FOREIGN PATENT DOCUMENTS

WO WO 96/38726 12/1996

OTHER PUBLICATIONS

J.M. Boulton, Mat. Res. Soc. Symp. Proc., vol. 180, pp. 773-777 (1990).*
J.A. Yanez et al, J. European Ceramic So., vol. 18, No. 11, pp. 1493-1502 (1998).*
G. Teowee et al, Materials Research Soc. Symposium Proceedings, vol. 180 (Better Ceram. Chem. 4), pp. 407-412 (1990).*
S Motakef et al, J. of Non-crystalline Solids, vol. 178, pp. 31-36 (1994).*

Gelest Corporation website: www.gelest.com/applications/HydrophilicMaterials.asp. "Silicon, Germanium, Tin and Metal-Organic Compounds".*
Butler et al., "Leaching in sol-gel-derived silica films for optical pH sensing", Journal of Non-Crystalline Solids, vol. 224, No. 3 (1998) pp. 249-258.
Frazier et al., "Characterization of protein-resistant dextran monolayers", Biomaterials, vol. 21, No. 9 (2000) pp. 957-966.
Haab et al., "Protein microarrays for highly parallel detection and quantitation of specific proteins and antibodies in complex solutions", Genome Biology, vol. 2, No. 2 (2001), pp. 1-13.
Harris, Polyethylene Glycol Chemistry, Biotechnical and Biomedical Applications, Plenus Press, 1992.
Kenney et al., "Structure-Property Relationships of Poly(vinyl Alcohol). III. Relationships between Stereoregularity, Crystallinity, and Water Resistance in Poly(vinyl Alcohol)", Journal of Polymer Science, vol. 4, Part A-1 (1966), pp. 679-698.
Lin et al., "Sol-gel glass as a matrix for chemical and biochemical sensing", TRAC, vol. 16, No. 4 (1997), pp. 200-211.
MacBeath et al., "Printing Proteins as Microarrays for High-Throughput Function Determination", Science, vol. 289, No. 5485 (2000), pp. 1760-1763.
Piehler et al., "A high-density poly(ethylene glycol) polymer brush for immobilization on glass-type surfaces", Biosensors & Bioelectronics, vol. 15 (2000), pp. 473-481.
Zelinski et al., "Sol-Gel Technology and the Nuclear Industry", http://www.wmsym.org//wm98/htmq/sess09/09-31/09-31.htm.
Lee, et al., "Protein-resistant coatings for glass and metal oxide surfaces derived from oligo(ethylene glycol)-terminated alkyltrichlorosilanes", Biomaterials, 1998 Elsevier Science Ltd., pp. 1669-1675.

* cited by examiner

*Primary Examiner*—Mary E. Ceperley

(57) ABSTRACT

The present invention relates to bio-molecule resistant surfaces for use in assays, particularly in assay devices such as arrays and microfluidic devices. The biomolecule resistant surface of the present invention are prepared by coating a substrate with hydrophilic terminated alkoxysilanes having formula (A):

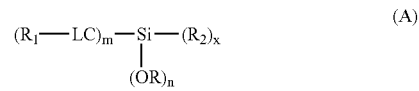

wherein R is an alkyl group of a size that allows for sufficient hydrolysis and n is 1, 2 or 3; $R_1$ is a hydrophilic moiety; LC is a $C_1$ to a $C_{10}$ linker chain consisting of a group selected from alkyl, aryl, alkaryl and aralkyl and m is 1, 2, or 3; $R_2$ is a $C_1$ to a $C_7$ alkyl group and x is 0, 1, or 2; and m+n+x is equal to 4.

17 Claims, No Drawings

BIOMOLECULE RESISTANT AND THEIR METHODS OF USE IN ASSAYS

FIELD OF THE INVENTION

The present invention relates to biomolecule resistant surfaces and methods of their use in assays, particularly in assays using arrays.

BACKGROUND OF THE INVENTION

A vast number of new drug targets are now being identified using a combination of genomics, bioinformatics, genetics, and high-throughput biochemistry. Genomics provides information on the genetic composition and the expression of an organism's genes. Bioinformatics uses computer algorithms to recognize and predict expressional patterns in DNA and structural patterns in polypeptides or proteins, defining families of related genes and proteins. Attempts to evaluate gene expression and to decipher biological processes, including those of disease processes and drug effects, have traditionally focused on genomics; however, genomics cannot provide a complete understanding of the cellular processes that are involved in disease processes and provides little or no information as to, for example, the relative abundance of different proteins in a cell, and the types of post-translational modifications present on proteins.

Proteomics offers a more direct and promising look at the biological functions of a cell and involves the qualitative and quantitative measurement of gene activity by detecting and quantitating expression at the protein level, rather than at the DNA or mRNA level. Proteomics also involves the study of non-genome encoded events including the post-translational modification of proteins, interactions between proteins, and the location of proteins within the cell. The structure, function, or levels of activity of the proteins expressed by a cell are also of interest. Generally, proteomics involves the study of part or all of the status of the total protein contained within or secreted by a cell. As many of the most important cellular processes are regulated by the protein status of the cell, not by the status of gene expression, a need exists to characterize proteins in high numbers in a similar manner as is done in genomics.

The number of chemical compounds available for screening as potential drugs is also growing dramatically due to recent advances in combinatorial chemistry, the production of large numbers of organic compounds through rapid parallel and automated synthesis. The compounds produced in the combinatorial libraries being generated will far outnumber those compounds being prepared by traditional, manual means, natural product extracts, or those in the historical compound files of large pharmaceutical companies. Both the rapid increase of new drug targets and the availability of vast libraries of chemical compounds create an enormous demand for new technologies that improve the screening process.

Current technological approaches for obtaining high-throughput screening of drugs and studying polypeptides or proteins function include multiwell-plate based screening systems, cell-based screening systems, microfluidics-based screening systems (in which interconnected fluid pathways and reaction chambers are engineered to provide a "lab on a chip"), and screening of soluble targets against solid-phase probes, e.g., synthesized drug components. Attachment of the target, rather than the probe, to a solid support in the form of an array is particularly promising and can be used to characterize proteins, protein-protein interactions and enzyme catalysis. These high-throughput screening assays are based on a variety of protein separation techniques followed by identification of the separated proteins. The most popular method for protein separation and identification is based on 2D-gel electrophoresis followed by "in-gel" proteolytic digestion and mass spectroscopy. Alternatively, Edman methods may be used for the sequencing.

The high-throughput method generates massive information on protein and peptide target function as well as the influence of synthetic drug on their function and expression level. In a complex biological system it is known that multiplexed proteins and small molecules are used for signal transduction and eventually are necessary for proper function of the system. Detection of numerous target proteins and polypeptide simultaneously is necessary for understanding biological pathways and diseases in such complex function. In order for the polypeptide or protein arrays to be effective, especially on such a large-scale, specific binding between the target and the probe is required, while non-specific binding has to be minimized.

Surface treatment is a key factor for the success of an assay in a high throughput format by reducing non-specific binding. Non-specific binding, or binding of biomolecules, such as polypeptides, proteins, and DNA, to the surface of the array, is a major problem in the design of surface binding assays and can be responsible for generating high background, a decrease in signal to noise ratio, and a decrease in specificity. In microfluidic devices, for example, non-specific binding can additionally lead to peak tailing during separation and a decrease in sensitivity.

Surface treatment with a blocking agent, such as bovine serum albumin (BSA) or milk proteins, can be used to block surface binding sites and reduce background due to non-specific binding. See, e.g., MacBeath & Schreiber, *Science*, 289: 1760–1763 (2000); Haab et al., *Genome Biology*, 2(2):1–13 (2001). However, such surface treatment with a blocking agent has various disadvantages. First, it requires a long incubation time for the surface to be covered with the blocking agent and the final surface has to be carefully stored in order to have fair reproducibility. Although blocking agents are relatively effective, there is a resulting decrease in signal to noise ratio due to the unintentional blocking of the probe molecules and the displacement of the blocking agent with the labeled target. In addition, protein-coated surfaces can obscure the probe molecules, particularly small probe molecules, such as aptamers and low-molecular-weight polypeptides and/or proteins. Although deposition of probe molecules on top of the blocking agent, e.g., BSA, is one possible solution, protein-protein interaction may decrease the binding between the target protein and probe molecule. Non-specific binding can also occur even after treatment with a blocking protein if a labeled protein displaces this blocking protein. For surfaces and channels that are part of microfluidic devices, coating with a non-essential blocking protein is also impractical due to the risk to bleeding, which can lead to a decrease in separation/detection efficiency, a shift in baseline, and contamination of the system.

Surface modification with hydrophilic molecules, such as polyethylene glycol (PEG) and dextran, is another approach that has been utilized to decrease non-specific binding of biomolecules, including proteins. See Piehler et al., *Biosensors & Bioelectronics* 15: 473–481 (2000); J. Milton Harris, ed., *Polyethylene Glycol Chemistry*, Plenum Press, New York, 1992; Frazier et al., *Biomaterials*, 21: 957–966 (2000). To yield a high quality surface resistant to non-specific binding, PEG and other hydrophilic molecules must be applied to a substrate with sufficient density and surface coverage, which has been proven to be a problem in prior approaches.

In one approach taken by Piehler, the surface of a substrate is modified by using glycidyloxipropylsilane to obtain an epoxy-moiety, which is then reacted with a reagent, followed by reaction with PEG. The epoxy moiety serves as an adhesive layer. Such a scheme requires tedious steps that increase the cost of the process and decrease its efficiency, particularly in light of a need for an adhesive layer. Additionally, an epoxy-moiety that serves as the adhesive layer is highly reactive, resulting in additional precautions that must be taken during the manufacturing process. Lee and Laibinis (*Biomaterials* 19: 1669–1675 (1998)) have taken another approach by coating a substrate with oligo (ethylene glycol)-terminated alkyltrichlorosilanes. This approach requires tedious synthetic steps at highly controlled anhydrous conditions because trichlorosilane is highly reactive and toxic. It also requires the protection of terminal functional groups, such as hydroxyl groups, to limit inter- or intra-molecular reaction with the trichlorosilane moiety. For many applications in which hydroxyl groups are needed for probe attachment through covalent linkage, an extra deprotection step is required. These factors make large-scale production difficult and costly.

Accordingly, there exists a need in the art for preparing an effective biomolecule resistant surface that can be prepared easily in a routine fashion with a minimal number of steps.

SUMMARY OF THE INVENTION

In one aspect, the present invention provides for biomolecule-resistant surfaces, and processes for their preparation, having a substrate coated with a hydrophilic terminated alkyl alkoxysilane having the formula (A):

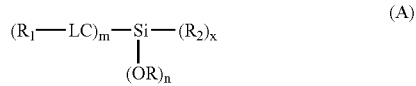

wherein R is an alkyl group of a size that allows for sufficient hydrolysis and n is 1, 2 or 3; $R_1$ is a hydrophilic moiety; LC is a $C_1$ to a $C_{10}$ alkyl, aryl, alkaryl or aralkyl linker chain and m is 1, 2, or 3; $R_2$ is a $C_1$ to a $C_7$ alkyl group and x is 0, 1, or 2; and m+n+x is equal to 4. The biomolecule resistant surfaces of the present invention can be used in conjunction with assays known in the art.

In another aspect, the present invention provides for assay devices such as microfluidic devices and arrays, as well as processes for making such assay devices, having a biomolecule resistant surface coated with a hydrophilic terminated alkyl alkoxysilane of the formula (A). In an additional aspect, the present invention provides a process for detecting or isolating a desired novel or known biomolecule, an example of which is a polypeptide, using the devices, particularly the arrays, of the present invention.

DETAILED DESCRIPTION OF THE INVENTION

The present invention provides for a new and facile polypeptide and/or protein and other biomolecule resistant surfaces on rigid or flexible substrates, and methods for their preparation, based on derivatized alkyl alkoxysilanes. The prepared surfaces are sufficiently stable and dense, and display minimal non-specific binding of biomolecules. The surfaces of the present invention are prepared by coating a substrate with hydrophilic terminated alkyl alkoxysilanes.

The present invention provides for a new and facile polypeptide and/or protein and other biomolecule resistant surfaces on rigid or flexible substrates, and methods for their preparation, based on derivatized alkyl alkoxysilanes. The biomolecule-resistant surface of the present invention can be prepared by (1) providing a substrate and (2) coating the substrate with the alkyl alkoxy silane of the formula (A):

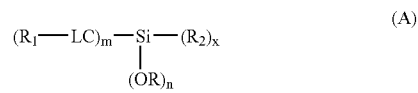

Preferably, R is of a size that allows for sufficient solubility and hydrolysis of the alkoxy group. To allow for sufficient hydrolysis, as used herein, R is substantially removed from the molecule, which, for example, allows for the formation of a colloidal-sol during sol-gel process, as described further below. Preferably, R is an alkyl group of seven carbons or less, and more preferably of one or two carbons.

As used herein, $R_1$ refers to a hydrophilic moiety that is substantially resistant to biomolecules. The substituents at the hydrophilic moiety should be substantially hydrophilic to minimize non-specific biomolecule binding, particularly for proteins. As used herein, moiety refers to a part of a molecule that has a certain characteristic, i.e., hydrophilicity. The moiety can have a single functional group, or a mixture of functional groups, i.e., ethers, esters, amides, among others.

One of skill in the art would appreciate that as the ratio of carbon to other elements, such as oxygen or nitrogen increases, hydrophilicity decreases. Preferably, $R_1$ has a maximum ratio of about 3:1 of carbon to oxygen or nitrogen. Most preferably, the ratio is about 1:1, which is the same ratio as in PEG (in case of PEG HO($CH_2CH_2O$)$_n$H, the ratio of C:O is about 2)

Preferably, the hydrophilic end is a polymer or an oligomer. Such an oligomer or polymer can be an oligo(ethylene glycol), dextran, poly(ethylene glycol), poly(vinyl alcohol). In another embodiment, the hydrophilic moiety is a small organic molecule. An example of a small organic molecule is glucose. The molecule of the present invention having glucose as a moiety can be purchased from Gelest (Morrisville, Pa.).

In a preferred embodiment, the hydrophilic moiety has an amino group at one end and a hydroxyl group at another end. The amino group allows for the attachment of the moiety to the linker chain while the hydroxyl group does the same for attachment of the probe molecule to the moiety. In another preferred embodiment, the hydrophilic moiety has amino groups at both ends. Functional groups at the end of the hydrophilic moiety can be derivatized to permit probe attachment, as described below.

The linker chain ("LC") refers to a $C_1$ to a $C_{10}$ alkyl, aryl, alkaryl or aralkyl group. More preferably, LC is a $C_1$ to a $C_5$ group and most preferably a propyl group. The term "alkyl alkoxysilane" exemplifies the molecule of the present invention, including when LC is a group other than an alkyl group.

The LC is attached to the hydrophilic moiety via a functional group such as an amine, an ether, an ester or an amide, among others. Although the LC is described for example, as an alkyl group, one of skill in the art would appreciate that the end of the LC can have other groups, such as an amino or a carboxyl group to allow for the attachment of the hydrophilic moiety. In a preferred embodiment, the hydrophilic moiety has terminal amino group, while the LC ends in a carboxyl group, allowing for attachment by forming an amide. In another preferred embodiment, the hydrophilic moiety has terminal hydroxyl group, while the LC ends with amino group, allowing for attachment by forming a urethane by transforming amino to cyanate.

As used herein, $R_2$ refers to a $C_1$ to a $C_7$ alkyl group. As the size of $R_2$ increases, the hydrophilicity of the molecule decreases, which is an undesirable effect. Preferably, $R_2$ is a methyl, ethyl or propyl group. As one of skill in the art would appreciate, the preferred length of $R_2$ can vary depending on the length of the hydrophilic moiety.

In a preferred embodiment, the molecule of the present invention has the following structure:

form Si—O—Si by losing one water molecule, thus resulting in the polymerization of silanols to form a colloidal structure. Silanol in the colloidal sol solution reacts with silanol groups on glass or oxidized silicon wafer to form covalent Si—O—Si. One of skill in the art would appreciate that, as a result of hydrolysis, the coat can lack the R group of the molecule.

The surface of a substrate can be treated to alter the adhesion of the substrate towards the coating by sol solution. Surface plasma treatment or oxidation on synthetic polymers can help generate oxidized groups such as hydroxyl or carboxyl groups, thus increasing adhesion of the hydrophilic coating on the surface. Silicon wafers, for example, are usually oxidized to generate silanol group. Butler et al., *Journal of Non-Crystalline Solid*, 224 (1998) 249–258 (hereinafter "Butler"). Butler immersed silicon wafers in a piranha solution to obtain a hydrated oxide surface on silicon with similar properties as that of glass. Other non-

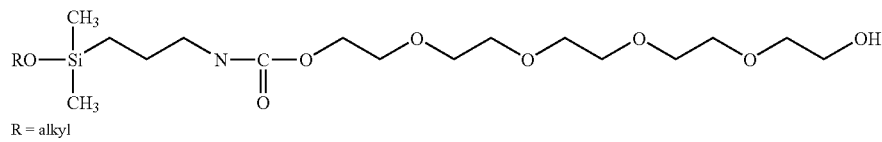

R = alkyl

The surfaces prepared by the molecule of the present invention are sufficiently stable and dense, and display minimal non-specific binding of biomolecules. The surfaces are prepared by coating a substrate with the molecule of the present invention. A preferred substrate is one capable of interacting with the molecules to substantially exhibit the molecules on its surface. The substrate can be flexible or rigid, transparent, translucent or opaque. In one embodiment, the substrate is flat, with minimal thickness compared to the surface area of the substrate. In another embodiment, the substrate has a three-dimensional shape that can be necessary for a particular process. U.S. Pat. No. 5,744,305 discloses that, in some instances, a substrate can also have a physical barrier, such a raised region or etched trenches.

In one embodiment, the substrate contains silicon groups. Examples of silicon based substrates include, e.g., glass and silicon wafer. In another embodiment, the substrate does not contain silicon. Examples of such substrates include, e.g., synthetic polymers, such as plastic, an example of which is polycarbonate, polyimide, polystyrene or polypropylene. Other examples of suitable substrates, including synthetic polymers, are disclosed in U.S. Pat. Nos. 6,329,209 and 5,688,642.

The substrate can be coated via any suitable means, e.g., mechanical, physical, electrical, or chemical means. For example, the alkyl alkoxysilanes of the present invention can be hydrolyzed under acidic or basic conditions to form a colloidal sol solution. Hydrolysis can be carried out in the presence of water and an acid/base catalyst in a single phase, as disclosed in U.S. Pat. No. 5,175,027. The solvent used for the hydrolysis step is preferably one in which the molecule of the present invention is substantially soluble in to form a solution. Preferred solvents are lower alkanols, such as ethanol, isopropanol, t-butanol, and lower ketones, such as acetone and methylethylketone.

Hydrolysis results in removal of "R" from the alkoxy group to form a silanol group (Si—OH). After hydrolysis, the silanol group readily reacts with other silanol groups to silicon based substrates can be treated in a similar fashion. For example, some plastic surfaces, such as polycarbonate, can be oxygen plasma treated in order to increase their adhesion with coated sol. See, e.g., U.S. Pat. No. 5,175,027.

In one embodiment, the substrate is dipped ("dip coated") into the sol solution. See, e.g., U.S. Pat. No. 5,856,016. In another embodiment, the substrate is spin coated with the sol solution. See, e.g., U.S. Pat. No. 6,300,144. The substrate is revolved from a fixed pivot point in the solution. Preferably, the substrate revolves at a speed from about 500 rpm to about 1500 rpm for a few minutes, with 1000 rpm being the most preferred speed. As the examples illustrate, surfaces spin coated at 1000 rpm for about two minutes are effective at resisting non-specific binding and are generally more uniform than dip coated surfaces. One of skill in the art would appreciate that the timing and the speed of the spin coating process can be changed without necessarily affecting the results, and experimental conditions can be adjusted to control resulting surface thickness.

In one embodiment, a covalent bond does not form between the molecules (sol colloids when using sol-gel) and the substrate after contact. Rather, other forces drive the molecules to coat the substrate. Such phenomena occur, for example, when using a plastic, such as polycarbonate.

In another embodiment, particularly when using a substrate with exposed silanol groups, the molecules (sol colloids when using sol-gel) form a covalent bond with exposed silanol groups on the substrate. A glass or an oxidized silicon wafer can be immersed in the solution so that surface silanol groups can react gradually with the solution of hydrolyzed molecules, or "sol solution." The silanol group of the molecule can react with silanol groups on the glass or oxidized silicon wafer to form covalent Si—O—Si bonds, or siloxanes. One of skill in the art would appreciate that, in some embodiments, a combination of covalent bonds and other forces can keep the molecules on the surface.

As one of skill in the art would appreciate, processes other than dipping or spinning in a solution can be used to coat the substrate with sol solution. These processes include gas vapor deposition, plasma enhanced gas vapor deposition, sputtering and thermal oxidation. These methods are well known in the art. See, e.g., U.S. Pat. Nos. 6,391,690, 4,516,527 and 4,287,661. In one embodiment, when using gas vapor deposition, the molecule is first hydrolyzed, then vaporized and contacted with the substrate. This technology is of importance in preparing surface coating on surfaces such as those of microfluidic devices at a well-controlled position and thickness. U.S. Pat. No. 6,150,285, for example, discloses the use of gas vapor deposition and sputtering to coat a substrate at predetermined locations.

For optimal result, curing follows the coating of the substrate with sol solution (Lin & Brown, *Trends in Analytical Chemistry* (1997) 16(4) 200–211). Curing conditions, such as time and temperature can affect the thickness and property of the film. Other factors affecting the thickness of the coat include silane concentration, speed and duration of spin coating and speed of dip coating. U.S. Pat. No. 5,175,027 discloses manipulation of the sol-gel process to change the thickness of a film.

The coating results in a dense/thin film. A thin film is optimal for preparation of a biomolecule resistant surface. The thickness density of the film can vary according to the use of the film and can be easily determined by one of skill in the art. The film is preferably less than about 20 nm in thickness.

The film used in the biomolecule resistant surface can have various organizations, layers and pattern. The film can be organized, such as in the form of a monolayer, or disorganized. As one of skill in the art would appreciate, the size of the LC connected to the hydrophilic moiety can play a role in whether a monolayer is formed. Larger alkyl groups lead to an increase in van der waals forces and an increase in the formation of monolayers. Large alkyl groups can, however, decrease the hydrophilicity of the surface, and thereby increasing nonspecific biding.

In another embodiment, the film comprises of multiple layer of coating. For example, a coating can comprise a bilayer or a monolayer on top of a self-assembled monolayer. To obtain multiple coatings, the coating process can be repeated.

The film can have a specific pattern. The substrate can be pre-patterned, limiting the reaction with hydrolyzed silanes only to specific areas on the substrate. See, e.g., U.S. Pat. No. 6,150,285. The substrate, for example, can be contacted with a sol solution at specific points using a robot, resulting in a patterned film.

Immobilization of a probe molecule to the surface results in a functional probe that can then be used to assay biomolecules. The probe molecules capture biomolecules. Such biomolecules include, e.g., oligo and polypeptides, nucleotides, saccharides, lipids and other natural biomolecules as well as recombinant and synthetic biomolecules, and their derivatives.

Probe molecules can be immobilized on the surface in various ways. See, e.g., U.S. Pat. Nos. 5,688,642 and 5,405,766. Terminal functional groups on the hydrophilic moiety can be chemically derivatized to facilitate the attachment of probe molecules via covalent bonds. For example, terminal hydroxyl groups of the hydrophilic moiety can be activated by carbonyl diimidazole, carbonyldi(1,2,4-triazole) or disuccinimidyl carbonate to form amino reactive compounds. Hydroxyl groups can also be oxidized to aldehydes that form strong C—N bonds with primary amines after reduction. Amino groups can be activated in a similar manner or transformed to isothiocyanate. A hydrophilic moiety with a terminal carboxyl group can be activated to its succinimidyl ester. Bi-functional cross-linking reagents, such as those disclosed in U.S. Pat. No. 5,412,087, can be utilized to covalently attach probe molecules onto the surface. There are many bi-functional cross-linking reagents commercially available for different functional group reactions. See, e.g., Pierce Catalog.

The group at the end of the hydrophilic moiety does not need to be activated if the silane used has a desired functional group at such location. For example, when using a silane molecule with an amino terminated hydrophilic moiety (such as a modified PEG), the probe can be put on the surface without the need to convert the hydroxyl group to an amino group. As one of skill in the art would appreciate, when putting a reactive group at the end of the hydrophilic moiety for probe attachment, the reactive group should be one that shows limited undesirable inter- and intra-cross reactivity during the coating process.

In many applications, the adjustment of hydrophilicity is important and can affect the balance between biomolecule attachment and non-specific binding properties of surfaces. Some applications require specific functional groups to be present at the end of the hydrophilic moiety, such as hydroxyl, amino, thiol or carboxyl. Mixing of alkyl alkoxysilanes with different hydrophilicity and functional groups is an easy method to fulfill the requirement, especially for large-scale production in which other chemical modifications are difficult or costly. Mixtures of alkyl alkoxysilanes with different hydrophilicity can be created by using different hydrophilic moieties.

In another embodiment, the probe molecules are dried on the biomolecule resistant surface. When biomolecules, such as proteins, are dried on the surface, they can not be washed off easily like non-dried probe molecules, allowing for a secure and stable probe. The probe is stable in such an instance even in the absence of surface functional group activation and covalent attachment. After immobilization of the probe molecules on the surface by drying, an assay can be carried out in a sealed chamber containing target biomolecules.

The probe molecules immobilized on the surface can then be used for assays. See, e.g., U.S. Pat. No. 6,316,205. Such assays include sandwich and competition assays. The assay devices include the dipstick format, the flow through format and the lateral flow format. An "assay device", as used herein, refers to any device containing immobilized or free probe molecules or other means for detecting the presence of biomolecules. See, e.g., U.S. Pat. Nos. 6,352,863 and 6,120,733. At least a portion of the assay device has the biomolecule resistant surface of the present invention. The biomolecule resistant surface can cover, for example, the reaction chamber of the device, with or without the probe molecules being immobilized on the biomolecule resistant surface.

A preferred assay device is a microfluidic device. A microfluidic device usually has one or more channels with at least one dimension less than 1 mm. See, e.g., U.S. Pat. Nos. 6,048,498 and 6,318,970.

The present invention provides for surface modification procedures that can be applied in conjugation with microfluidic technology. Chambers and channels of a microfluidic device can be specifically modified with the above alkyl alkoxysilane to ensure that separation channels or analysis areas have low non-specific binding with biomolecules. The surface on a microfluidic device can be modified in a similar way as those described above. The chambers and channels can also be selectively modified for different applications.

A particularly preferred assay device is an array. See, e.g., U.S. Pat. No. 6,329,209. The probe molecules can be printed on arrays by techniques well known in the art. Such technologies, include, but are not limited to, thermal inkjet printing, piezo printing, laser ablation, electrodeposition, physical and chemical vapor deposition, photolithography, and wet chemical and dry etching. Related technologies, such as injection molding and LIGA (X-ray lithography, electrodeposition, and molding), are also included.

The arrays placed on the substrate/surface can have the same or different probe molecules. Often, it is desirable to have arrays that exhibit different probe molecules. The diversity allows for an automated process in which more than one kind of biomolecule can be screened simultaneously, thus increasing efficiency, saving time and decreasing the necessary amount of a biological sample. Such speed is especially important in proteomics, in which many unidentified proteins need to be selected and characterized. General mapping of protein expression level and interaction pattern are also important for drug screen and development, as well as for disease identification. When using different probe molecules in each array, the arrays can be precisely put on the substrate, and their position identified to aid in the characterization of the target. An automated robot as well as other printing techniques can be used to put the arrays precisely on the substrate or the coating of the substrate. The biomolecule resistant surface of each array can also exhibit different levels of hydrophilicity. In another embodiment, the arrays have backgrounds exhibiting different levels of hydrophilicity and/or have probes with different probe molecules.

As one of skill in the art would appreciate, each array can be placed at regular intervals on the surface or on the substrate next to the surface. When placing probes next to the surface on the substrate, the dimensions or the number of arrays does not necessarily change, but preferably, the probes are put a sufficient distance away from the coating to minimize occlusion. One of skill in the art would appreciate that a change in the pattern in which the probes are laid, in particular, their size and distance from each other, would not necessarily change the results. U.S. Pat. No. 6,329,209, for example, provides guidance on the number of arrays and probes, and their patterns.

The probes of the arrays are used to specifically bind to biomolecules. The probes are preferably covalently immobilized on the array, either directly or indirectly. The probe molecule used can be, for example, an antibody for a particular polypeptide and/or a protein. Proteins from a sample, such as one prepared by disruption of cells, can be screened simultaneously by contacting them with the multiple probe molecules immobilized on the surface. Arrays can also be used for purposes other than protein-protein selection. For example, a protein can be used as a probe molecule to screen for a small molecule, an enzyme for screening a substrate, or a specific sequence of DNA can be used to probe nucleic acid with a complementary sequence.

A fluorescent tag can then be used to identify binding. See, e.g., U.S. Pat. No. 6,339,172. Binding can be determined by using different colored tags. One of skill in the art would appreciate that binding can be detected with direct and indirect means, and other assays. For example, an antibody can be used for detecting binding by labeling the antibody with biotin, followed with the use of fluorescently labeled streptavidin to bind to biotin on the antibody. Multiple biotin molecules may be incorporated on the antibody, resulting in amplification of the signal.

Another technique from DNA gene expression array can be applied to detect proteins. This technique labels normal sample with one colored dye (e.g., Cy3) and disease sample with another colored dye (e.g., Cy5). The mixture of labeled normal and disease sample is applied to an array with immobilized probe molecules. The combination of colors, such as green (Cy3) and red (Cy5), creates a yellow color if the diseased and normal samples express the assayed protein at the same level. Any up regulation or down regulation of the protein in the diseased sample would result in deviation from yellow towards the color of the dye that is present at a higher concentration. The dyes are then swapped to verify the results ("dye swap") and offset any labeling error. Thus, the assay allows for identifying up and down regulated proteins. These techniques can also be used with assay devices.

Preferably, the probe molecule used maintains its natural structure while immobilized on the surface. Maintenance of biological function aids in selecting desired biomolecules that naturally bind to the probe molecule. Proteins have four different levels of structure. The tertiary structure of a protein plays an important role in specific binding. A lack of tertiary structure can disrupt the binding site. A problem with protein arrays is their high sensitivity of proteins. Proteins can denature at solid-liquid and liquid-air interfaces, which is a considerable problem when using a flat surface, due to the large surface area compared to the thickness of the film.

Preferably, the conditions used during screening are such that the proteins do not denature or substantially lose their tertiary structure. In one embodiment, the arrays are integrated into flow chambers to keep proteins in an aqueous solution at all times. When using nucleic acid, fewer precautions need to be taken since nucleic acids are stable even under relatively harsh conditions.

However, it has surprisingly been found that proteins can be dried on the surface and still be effective as probe molecules. Even though the proteins, such as antibodies, lose some structure, they still maintain sufficient structure to be effective. The dried proteins contact with the target biomolecules and bin with them in a buffered solution.

The following examples further illustrate the invention:

EXAMPLES

Example 1

The present example demonstrates coating of a glass substrate with N-(triethoxysilylpropyl)-O-polyethylene oxide urethane (POPTES) to prepare POPTES surface.

Commercial glass slides were cleaned in 2% RBS/DI water under sonication at 60° C. for 2 hours and then rinsed with water and immersed in concentrated nitric acid for 10 min. After rinsing thoroughly with deionized water, the slides were dried under nitrogen flow.

Four mL of N-(triethoxysilylpropyl)-O-polyethylene oxide urethane (POPTES, the surface made with reagent was referred as POPTES surface) (from Gelest) was dissolved in 186 mL of isopropanol. Ten mL of 2 N hydrochloric acid was added to adjust the pH to 1. The mixture was stirred at room temperature for 5 min. Cleaned glass slides were immersed in the solution for 2–3 days at room temperature under constant stirring. After reaction, the slides were rinsed twice with ~200 mL isopropanol and dried under nitrogen flow. The slide was cured at room temperature for 2 days before further testing.

Good surface coverage was demonstrated by atomic force microscopic (AFM) measurement (10 micro×10 micro) and fluorescence measurement (cross the slide) under Agilent scanner (any large surface defects can be detected). Intrinsic fluorescence (background) of such modified surface is comparable with commercial slides for DNA arrays under Agilent Scanner.

Example 2

The present example demonstrates spin coating of a glass substrate with N-(triethoxysilylpropyl)-O-polyethylene oxide urethane to prepare POPTES surface.

Commercial glass slides were cleaned in 2% RBS/DI water under sonication at 60° C. for 2 hours and then rinsed with water and immersed in concentrated nitric acid for 10 min. After rinsing thoroughly with deionized water, the slides were dried under nitrogen flow.

Four mL of N-(triethoxysilylpropyl)-O-polyethylene oxide urethane (POPTES, the surface made with reagent was referred as POPTES surface) (from Gelest) was dissolved in 186 mL isopropanol. 10 mL of 2 N hydrochloric acid was added to reduce the pH to 1. Spin coating was carried out at 1000 rpm for two minutes followed by curing at 100° C. under vacuum for 3 hours. The spin coated POPTES surface was very hydrophilic.

Good surface coverage was demonstrated by atomic force microscopic (AFM) measurement (10 micro×10 micro) and fluorescence measurement (cross the slide) by Agilent scanner (any large surface defects can be detected). Intrinsic fluorescence (background) of such modified surface is comparable with commercial slides for DNA arrays under Agilent Scanner.

Example 3

The present example demonstrates protein non-specific binding property of POPTES surface and comparison with other types surfaces. The polylysine slides were prepared using the method disclosed in Haab et al., *Genome Biology*, 2(2), 1–13 (2001) with minor modifications. POPTES surfaces prepared as in Example 1 and Example 2, and ALTO surface prepared by reacting deprotonated tetra(ethylene glycol) with a monolayer of alkyl bromide predeposited on the surface. The optimal coverage with tetra(ethylene glycol) was about 30%.

Cy3-BSA from reaction between Cy3-NHS (from Amersham BioScience) and BSA (from Sigma) in carbonate buffer was used for testing. The dye to protein ratio was about 5 for purified conjugate. The labeled protein was spotted on the surface of the slides at following 4 concentrations 100 ug/mL, 50 ug/mL, 25 ug/mL and 12.5 ug/mL. The spotting volume was 1 uL. After spotting the slides was kept in humidified chamber for 1 hour at room temperature under dark. The droplets were withdrawn with a pippetor before they were put into washing buffer.

Washing buffer was prepared as follows: 1 liter PBS buffered solution was prepared by using 140 mM NaCl, 4.3 mM $Na_2HPO_4*7H_2O$, 1.4 mM $KH_2PO_4$, with 0.913 mL Tween-20 being added. The solution described herein is set forth in detail in Haab et al., supra.

The incubated slides were washed in the above buffer for 25–30 min at room temperature under constant stirring. The slides were then washed with deionized water four times for about 10 min each at room temperature and were dried under nitrogen flow.

Scans of the slides were taken with an axon scanner GenePix 4000A at PMT voltage 500 V. POPTES surface prepared by gave the least fluorescence signal at 536 nm. The signal was buried within the background. ALTO surface gave signal range of 3000–10,000. On polylysine surface the signal ranges from saturating detector to 20,000 (signal saturation at 65,000). POPTES surfaces prepared by Example 1 and Example 2 gave similar results within experimental error.

Example 4

The present example demonstrates a comparison of surfaces washed with PBS-. 1% Tween-20 in the presence of non-fat milk as compared to previous Example where milk was not used.

Example 3 was repeated with the following modifications: the slides were washed with 6 mL non-fat milk in 196 mL of PBS/0.1% Tween-20. POPTES surfaces showed the least non-specific binding. The intensity is also similar to the corresponding slides washed without milk in the washing solution.

Example 5

The present example demonstrates activation of POPTES using disuccinimidyl carbonate.

The hydroxyl groups on the surface were activated with disuccinimidyl carbonate (DSC) by the following procedure. DSC (2.56 g) was dissolved in 200 ml anhydrous acetonitrile (0.05 M) and triethylamine (2.78 ml) was added. POPTES surface was immersed in solution at room temperature under constant stirring for 4 hours. The slides were then rinsed twice with 200 anhydrous acetonitrile and dried under nitrogen flow.

The slides were spotted with 100 ug/ml, 50 ug/ml, 25 ug/ml, 12.5 ug/ml of BSA-Cy3 solution with a pH of about 9. The slides were then incubated at room temperature for 1.5 hours in a humidified chamber. They were washed with 5.7 mM PBS at pH 7.4 and 1% Tween-20 for 25 min. and then four times with deionized water for about 10 min. each. After drying with $N_2$ flow, the slides were scanned with Axon GenePix 4000A scanner at PMT 500 V.

Activated groups on the surface react with primary amines on proteins and formed covalent linkages, with a very intense fluorescence signal observed.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. Detailed descriptions of conventional methods relating to manipulations of DNA, RNA, and proteins can be obtained from numerous publications, including Sambrook, J. et al., (1989) *Molecular Cloning: A Laboratory Manual*, $2^{nd}$ ed., Cold Spring Harbor Laboratory Press. All references mentioned herein are incorporated in their entirety.

What is claimed is:

1. biomolecule-resistant surface comprising a substrate coated with a hydrophilic terminated alkyl alkoxysilane having the formula (A):

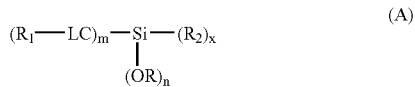

(A)

wherein is an alkyl group of a size that allows for hydrolysis of the alkoxy group and n is 1,2 or 3; $R_1$ is a hydrophilic moiety that is a small organic molecule; LC is a $C_1$ to a $C_{10}$ linker chain consisting of a group selected from alkyl, aryl, alkaryl and aralkyl and m is 1, 2, or 3; $R_2$ is a $C_1$ to a $C_7$ alkyl group and x is 0, 1, or 2; and m+n+x is equal to 4.

2. The surface of claim 1, wherein the substrate is selected from the group consisting of glass, silicon and synthetic polymer.

3. The surface of claim 1, wherein R is a $C_1$ to a $C_7$ alkyl group.

4. The surface of claim 1, wherein the LC is a $C_1$ to a $C_5$ alkyl group.

5. The surface of claim 4, wherein the alkyl group is a propyl group.

6. The surface of claim 1, wherein $R_2$ is a $C_1$ to a $C_3$ alkyl group.

7. The surface of claim 6, wherein $R_2$ is a methyl group.

8. An assay device comprising the surface of claim 1.

9. The device of claim 8, wherein the device is a microfluidic device.

10. The device of claim 8, wherein the device is an array.

11. A process for preparing an array comprising:
   immobilizing probe molecules on or next to the surface of claim 1 via covalent bonds with a reactive group on the hydrophilic moiety.

12. The array prepared by the process of claim 11.

13. An array comprising probe molecules immobilized on or next to the surface of claim 1.

14. The array of claim 13, wherein the probe molecules are proteins.

15. A process for detecting a desired novel or known biomolecule comprising:
   a) contacting a biomolecule with the array of claim 13 to obtain binding between the biomolecule and probe molecules of the ray; and
   b) detecting binding of the biomolecule to the array, whereby detection of binding is correlated with the presence/amount of the biomolecule.

16. A process for isolating a desired novel or known biomolecule comprising separating the bound biomolecule from the array of claim 15, thereby isolating the desired biomolecule.

17. A process for identifying a novel or known biomolecule comprising analyzing the separated biomolecules of claim 16.

* * * * *